United States Patent
Gopal et al.

(10) Patent No.: US 11,883,798 B2
(45) Date of Patent: Jan. 30, 2024

(54) SELECTIVE OXIDATION CATALYST AND A METHOD FOR OXIDIZING $C_2$ HYDROCARBONS IN THE PRESENCE OF THE SELECTIVE OXIDATION CATALYST

(71) Applicant: SABIC Global Technologies B.V., Bergen op Zoom (NL)

(72) Inventors: Srikant Gopal, Riyadh (SA); Turki Al-Smari, Riyadh (SA)

(73) Assignee: SABIC GLOBAL TECHNOLOGIES B.V., Bergen OP Zoom (NL)

( * ) Notice: Subject to any disclaimer, the term of this patent is extended or adjusted under 35 U.S.C. 154(b) by 219 days.

(21) Appl. No.: 17/250,538

(22) PCT Filed: Sep. 17, 2019

(86) PCT No.: PCT/IB2019/057813
§ 371 (c)(1),
(2) Date: Feb. 1, 2021

(87) PCT Pub. No.: WO2020/058843
PCT Pub. Date: Mar. 26, 2020

(65) Prior Publication Data
US 2021/0316279 A1 Oct. 14, 2021

Related U.S. Application Data

(60) Provisional application No. 62/732,505, filed on Sep. 17, 2018.

(51) Int. Cl.
*B01J 23/652* (2006.01)
*B01J 37/04* (2006.01)
*B01J 37/08* (2006.01)
*B01J 6/00* (2006.01)
*B01J 37/03* (2006.01)
*C07C 51/16* (2006.01)

(52) U.S. Cl.
CPC ........... *B01J 23/6525* (2013.01); *B01J 6/001* (2013.01); *B01J 37/031* (2013.01); *B01J 37/04* (2013.01); *B01J 37/08* (2013.01); *C07C 51/16* (2013.01)

(58) Field of Classification Search
CPC ............. B01J 23/6525; B01J 23/6482; B01J 23/6484; B01J 23/648; B01J 37/031; B01J 37/04; B01J 37/08; B01J 6/001; C07C 5/16
USPC ........................................................ 502/312
See application file for complete search history.

(56) References Cited

U.S. PATENT DOCUMENTS

| | | | |
|---|---|---|---|
| 6,030,920 A | * | 2/2000 | Karim ................. B01J 23/6525 502/313 |
| 6,034,270 A | | 3/2000 | Borchert et al. |
| 6,143,921 A | | 11/2000 | Karim et al. |
| 6,143,928 A | | 11/2000 | Karim et al. |
| 6,194,610 B1 | | 2/2001 | Borchert et al. |
| 6,274,764 B1 | | 8/2001 | Karim et al. |
| 7,015,355 B2 | | 3/2006 | Zeyss et al. |
| 2014/0235893 A1 | | 8/2014 | Al-Zeghayer et al. |

FOREIGN PATENT DOCUMENTS

| | | |
|---|---|---|
| CN | 1360565 A | 7/2002 |
| CN | 101041135 A | 9/2007 |
| CN | 102056662 A | 5/2011 |
| DE | 19630832 | 2/1998 |
| EP | 0294845 | 12/1988 |
| WO | WO 2001/90039 | 11/2001 |
| WO | WO 2009/151255 | 12/2009 |
| WO | WO 2013/148006 | 10/2013 |

OTHER PUBLICATIONS

Al-Zeghayer, Yousef S., "Partial Oxidation of Ethane to Acetic Acid Catalyzed by MoVNbPd Catalyst Supported on Titania" *International Journal of Chemical Engineering and Applications* 2014, 5(1), 50-57.
International Search Report and Written Opinion issued in Corresponding PCT Application No. PCT/IB2019/057813, dated Nov. 26, 2019.
Li, Xuebing and Enrique Iglesia, "Kinetics and Mechanism of Ethane Oxidation to Acetic Acid on Catalysts Based on Mo—V—Nb Oxides" *J. Phys. Chem. C* 2008, 112(38), 15001-15008.
Li, Xuebing and Enrique Iglesia, "Synergistic Effects of $TiO_2$ and Palladium-Based Cocatalysts on the Selective Oxidation of Ethene to Acetic Acid on Mo—V—Nb Oxide Domains" *Angew. Chem. Int. Ed.* 2007, 46, 8649-8652.
Roussel et al., "MoV-based catalysts in ethane oxidation to acetic acid: Influence of additives on redox chemistry" *Catalysis Today* 2009, 141, 288-293.
Search Report for CN Application No. 2019800597808, dated Feb. 1, 2023, 3 pp.

* cited by examiner

*Primary Examiner* — Yong L Chu
(74) *Attorney, Agent, or Firm* — WOMBLE BOND DICKINSON (US) LLP

(57) ABSTRACT

Methods of producing a catalyst for oxidation of $C_2$ hydrocarbons and methods of using the catalyst are disclosed. Molybdenum, vanadium, and niobium metal or metal containing compounds are used to form a slurry in water. After agitating the slurry for at least 15 minutes, palladium or a palladium containing compound is added to the slurry. After further agitation, a precipitate is collected, dried and calcined to obtain an active catalyst, with palladium primarily distributed on a surface of the catalyst. The active catalyst is capable of catalyzing the conversion of $C_2$ hydrocarbons into acetic acid.

20 Claims, 1 Drawing Sheet

SELECTIVE OXIDATION CATALYST AND A METHOD FOR OXIDIZING C₂ HYDROCARBONS IN THE PRESENCE OF THE SELECTIVE OXIDATION CATALYST

CROSS REFERENCE TO RELATED APPLICATIONS

This application is a national phase application under 35 U.S.C. § 371 of International Application No. PCT/IB2019/057813 filed Sep. 17, 2019, which claims priority to and the benefit of U.S. Provisional Application No. 62/732,505, filed Sep. 17, 2018, all of which are incorporated herein by reference in their entirety.

FIELD OF INVENTION

The present invention generally relates to a catalyst for oxidation of $C_2$ hydrocarbons. More specifically, the present invention relates to a mixed metal oxide catalyst for oxidizing ethane to form acetic acid.

BACKGROUND OF THE INVENTION

Acetic acid is a chemical reagent used in the production of plastic bottles, photographic films, polyvinyl acetate (for wood glues), and synthetic fibers and fabrics. Acetic acid is also commonly used as a cleaning agent, an acidity regulator for food, and a condiment.

There are several conventional methods of producing acetic acid in the chemical industry. One of the most commonly used methods is carbonylation of methanol. In this process, methanol, carbon monoxide and hydrogen react over a catalyst at a temperature higher than 180° C. to form acetic acid and water. Bacterial fermentation is another process widely used for acetic acid production when acetic acid is used in vinegar or as a food acidity regulator.

Gas phase oxidation of $C_2$ hydrocarbon is another process for acetic acid production. In this process, ethane is directly oxidized to form ethylene and then acetic acid, in a single reactor having a single catalyst bed. This process directly uses low value and low toxicity reactant ethane to produce acetic acid. Therefore, it has low environmental impact. However, so far, the method has shown very limited production rate. The production process often ends with production of ethylene rather than of acetic acid, which further oxidation would produce.

Overall, while methods of producing acetic acid exist, the need for improvements in this field persists in light of at least the aforementioned drawbacks of the methods.

BRIEF SUMMARY OF THE INVENTION

A solution to at least some of the above mentioned problems associated with the production process for acetic acid has been discovered. The solution resides in a catalyst for oxidation of ethane to form acetic acid. Notably, the catalyst has at least 50 ppm of Pd distributed on the surface thereof. This can be beneficial for at least improving the conversion rate of ethylene to acetic acid after ethane is first oxidized to ethylene, solving the problem of low conversion rate of ethylene to acetic acid in conventional methods. Therefore, the methods of the present invention provide a technical solution to at least some of the problems associated with the currently available methods for producing acetic acid mentioned above.

Embodiments of the invention include a catalyst produced by a process that comprises combining each of a molybdenum, vanadium, and niobium metal or metal-containing compound in water to form a slurry. In some embodiments, a complexing agent may be added to aid in metal or metal-containing compound dissolution. An exemplary, non-limiting complexing agent is oxalic acid. In some embodiments, the process entails preparing an aqueous solution of each of a molybdenum, vanadium, and niobium metal or metal-containing compound, and combining the solutions and initiating precipitation to form a slurry. In some aspects, the slurry is agitated for a period of at least 15 minutes. After at least 15 minutes of agitating the slurry, palladium or a palladium-containing compound, preferably a solution comprising a palladium-containing compound is added to the slurry. The delayed addition of palladium allows precipitation of the molybdenum, vanadium, and niobium metal or metal-containing compounds to proceed to completion or near-completion prior to addition of the palladium component. Successive addition of palladium provides most of the palladium on the surface of precipitated material, thereby making the palladium more accessible to reactants. Delayed palladium addition prevents precipitation of molybdenum, vanadium, and niobium oxides over the palladium, thereby limiting or preventing palladium encapsulation. Because the present method favors placement of the highly reactive palladium component on the exterior surface of molybdenum, vanadium, and niobium oxides precipitates, the amount of the more costly palladium component can be minimized. The process further comprises collecting, drying, and calcining the slurry to obtain an active catalyst.

Embodiments of the invention include a method for oxidizing a $C_2$ hydrocarbon. The method comprises combining each of a molybdenum, vanadium, and niobium metal or metal-containing compound in water to form a slurry. The method further comprises agitating the slurry for a period of time of at least 15 minutes. The method further comprises after at least 15 minutes of agitating the slurry comprising molybdenum, vanadium, and niobium, adding palladium or a palladium-containing compound to the slurry. The method further comprises collecting, drying, and calcining the slurry to obtain an active catalyst. The method further comprises placing the active catalyst in a reactor and reacting the $C_2$ hydrocarbon with an oxidant in the presence of the active catalyst to produce an oxidized hydrocarbon. The oxidant may comprise steam, oxygen, or combinations thereof.

Embodiments of the invention include a method for oxidizing ethane to acetic acid. The method includes combining each of a molybdenum, vanadium, and niobium metal or metal-containing compound in water to form a slurry. The method further comprises agitating the slurry comprising molybdenum, vanadium, and niobium for a period of time of at least 15 minutes. The method further comprises after at least 15 minutes of agitating the slurry comprising molybdenum, vanadium, and niobium, adding palladium or a palladium-containing compound to the slurry. The method further comprises collecting, drying, and calcining the slurry to obtain an active catalyst. The method further comprises placing the active catalyst in a reactor and reacting ethane with an oxidant in the presence of the active catalyst to produce an oxidized hydrocarbon.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component. The phrase "delta ethane" is be defined as the difference between inlet and outlet ethane concentrations.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, $C_2$ hydrocarbon oxidation can be performed in a single reactor using mixed metal oxides as a catalyst. However, the conventional mixed metal oxides have limited efficiency for converting $C_2$ hydrocarbon oxidation into acetic acid. The present invention provides a solution, at least in part, to the problem. The solution is premised on a method that produces a catalyst that comprises molybdenum, vanadium, niobium and palladium metals or metal-containing compounds. In this method, palladium and/or palladium containing compounds are added into a slurry of molybdenum, vanadium, and niobium metals or metal-containing compounds after agitating the slurry for at least 15 minutes such that palladium is primarily distributed on the surface of the catalyst. Therefore, the palladium in the catalyst of the present invention has sufficient contact with the reactant to convert ethylene to acetic acid, resulting in an increased efficiency of producing acetic acid. These and other non-limiting aspects of the present invention are discussed in further detail in the following sections.

A. Methods of Producing a Catalyst for Oxidation of $C_2$ Hydrocarbon

Figure 1:
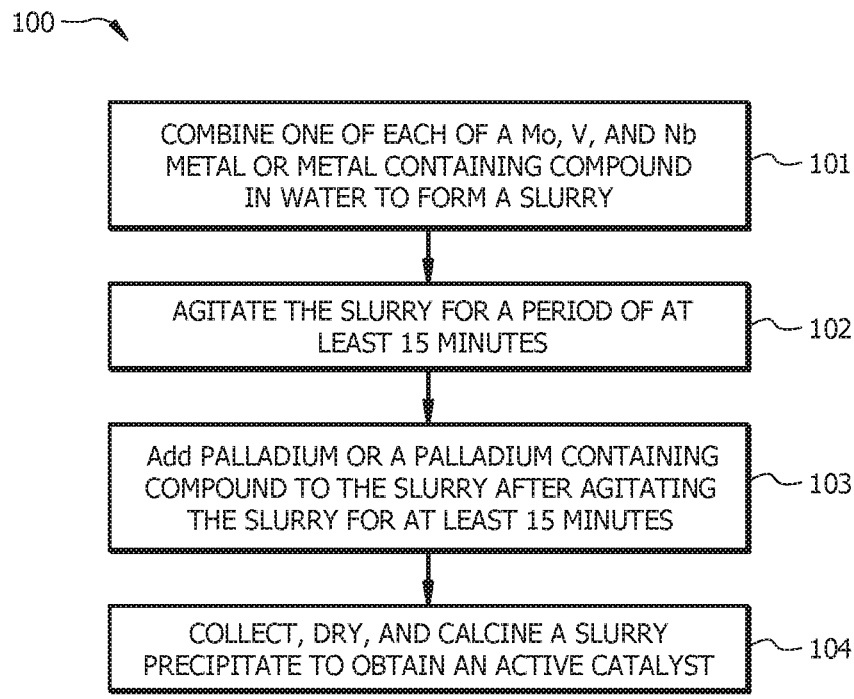
FIG. 1 shows a schematic flowchart of a process of producing a catalyst, according to embodiments of the invention.

As shown in FIG. 1, embodiments of the invention include method 100 of producing a catalyst for oxidation of $C_2$ hydrocarbon. According to embodiments of the invention, method 100 may include combining each of a molybdenum, vanadium, and niobium metal or metal containing compound in water to form a slurry (step (a)), as shown in block 101. In embodiments of the invention, the molybdenum metal containing compound comprises an ammonium salt, such as ammonium heptamolybdate, sodium molybdate, ammonium orthomolybdate, or ammonium paramolybdate, or an organic acid salt of molybdenum such as an acetate, oxalate, mandelate, glycolate, or a combination thereof. In embodiments of the invention, vanadium metal-containing compound is ammonium metavanadate, sodium metavanadate, sodium decavanadate, or sodium orthovanadate, or an organic salt of vanadium such as an acetate, oxalate, tartrate, or a combination thereof. In embodiments of the invention, the niobium metal containing compound comprises lithium niobate, potassium niobate, strontium barium niobate, niobium oxalate, niobium oxide, niobium hydrate oxide or a combination thereof. In embodiments of the invention, the slurry is formed via precipitation of molybdenum, vanadium, and niobium metal or metal containing compounds.

According to embodiments of the invention, method 100 may further include agitating the slurry for a period of time of at least 15 minutes, as shown in block 102 (step (b)). In embodiments of the invention, agitating at block 102 may be performed at a temperature of 70 to 100° C. and all ranges and values there between.

According to embodiments of the invention, as shown in block 103, method 100 may further include adding palladium or a palladium-containing compound to the slurry after at least 15 minutes of agitating the slurry comprising molybdenum, vanadium, and niobium (step (c)). In embodiments of the invention, substantially all molybdenum, vanadium, and niobium from step (a) may be precipitated before adding palladium or a palladium-containing compound at block 103.

In embodiments of the invention, the palladium-containing compound may include a palladium salt, a palladium complex, or palladium on a support, such as $Pd/SiO_2$, $Pd/Al_2O_3$, $Pd/TiO_2$, or a combination thereof. In embodiments of the invention, the slurry may be agitated after adding palladium or the palladium-containing compound therein. In embodiments of the invention, the slurry may be agitated for 5 to 200 minutes after adding the palladium or the palladium containing compound therein.

In embodiments of the invention, method 100 may further include collecting, drying, and calcining the slurry to obtain an active catalyst (step (d)), as shown in block 104. In embodiments of the invention, drying at block 104 may include spray drying, air drying, drum drying, vacuum drying, combinations thereof, or other drying methods known to those of skill in the art. The drying at block 104 may be performed at a drying temperature of 80 to 300° C. and all ranges and values there between. In embodiments of the invention, calcining at block 104 may have a calcination temperature of 100 to 400° C. and all ranges and values there between. A temperature ramp may be in a range of 0.1 to 5° C./min and all ranges and values there between. The temperature ramp may include multiple temperature-ramping and temperature-holding steps. A calcination duration at block 104 may be in a range of 1 to 24 hrs and all ranges and values there between. In embodiments of the invention, the calcining at block 104 may be conducted within ambient environment comprising air, nitrogen, or combinations thereof.

In embodiments of the invention, 10 to 500 ppm, preferably 50 to 300 ppm of palladium from the palladium metal or metal containing compound is distributed on a surface of the active catalyst. According to embodiments of the invention, the active catalyst may have a formula of $Mo_xN_yNb_zPd_nO_m$, where x is in a range of 1 to 5, y is in a range of greater than 0 to 0.5, z is in a range of 0.01 to 0.5, n is in a range of greater than 0 to 0.2 and m is a number determined by the valence requirements of the other elements in the composition.

In embodiments of the invention, the active catalyst may have a surface area in a range of 15 to 40 $m^2/g$ and all ranges and values there between. According to embodiments of the invention, the active catalyst may have an absolute porosity of 0.1 to 0.5 ml/g and all ranges and values there between. In embodiments of the invention, the active catalyst may not include a support material.

B. Methods for Oxidizing a $C_2$ Hydrocarbon

Figure 2:
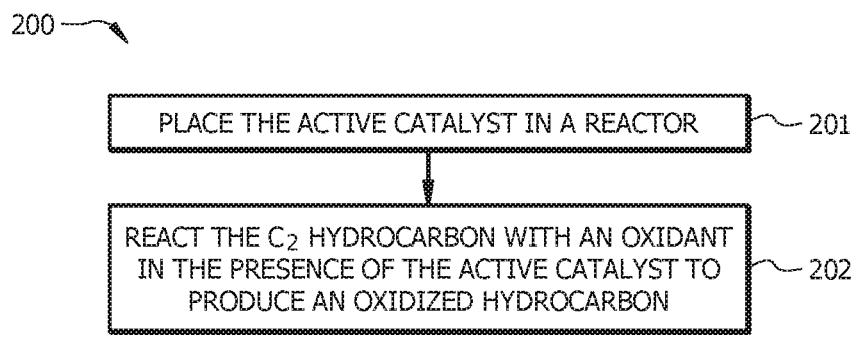
FIG. 2 shows a schematic flowchart of a method for oxidizing a $C_2$ hydrocarbon, according to embodiments of the invention.

As shown in FIG. 2, embodiments of the invention include method 200 for oxidizing a $C_2$ hydrocarbon. Method 200 may be implemented by the active catalyst produced via method 100, as shown in FIG. 1. According to embodiments of the invention, method 200 may include placing the active catalyst produced via method 100 in a reactor, as shown in block 201. In embodiments of the invention, the reactor may include a fixed bed reactor, for example, a multi-tubular reactor having catalyst positioned within the tubes, or a fluidized bed reactor.

According to embodiments of the invention, method 200 may further include reacting the $C_2$ hydrocarbon with an oxidant in the presence of the active catalyst to produce an oxidized hydrocarbon, as shown in block 202. In embodiments of the invention, the $C_2$ hydrocarbon may include ethane, ethylene, or combinations thereof. The oxidized hydrocarbon may be acetic acid, in embodiments. In embodiments of the invention, the oxidant at block 202 may include oxygen gas or steam.

In embodiments of the invention, the reacting at block 202 may have a reaction temperature in a range of 200 to 320° C. and all ranges and values there between. The reacting at block 202 may further include a reaction pressure of 5 to 40 bar and all ranges and values there between. A weight hourly space velocity at block 202 may be in a range of 1,000 to 10,000 $hr^{-1}$ and all ranges and values there between. In embodiments of the invention, the reacting at block 202 may include an oxygen concentration in the range of 1 to 10 mol. %, and all ranges and values there between.

A selectivity for acetic acid for the reacting step at block 202 may be in a range of 10 to 100 and all ranges and values there between. In embodiments of the invention, an effluent from the reactor may include 0.01 to 5 mol. % acetic acid and all ranges and values there between. In some aspects, delta ethane may range from 0.1 to 10 mol. %, preferably from 0.1 to 6 mol. %. In embodiments of the invention, method 200 may further include separating the effluent from the reactor to produce purified acetic acid.

Although embodiments of the present invention have been described with reference to blocks of FIGS. 1 and 2, it should be appreciated that operation of the present invention is not limited to the particular blocks and/or the particular order of the blocks illustrated in FIGS. 1 and 2. Accordingly, embodiments of the invention may provide functionality as described herein using various blocks in a sequence different than that of FIGS. 1 and 2.

In the context of the present invention, at least the following 19 embodiments are described. Embodiment 1 is a catalyst produced by a process. The process includes: (a) combining each of a molybdenum, vanadium, and niobium metal or metal-containing compound in water to form a slurry, (b) agitating the slurry for a period of time of at least 15 minutes, (c) after at least 15 minutes of agitating the slurry containing molybdenum, vanadium, and niobium, adding palladium or a palladium-containing compound to the slurry, and (d) collecting, drying, and calcining the slurry to obtain an active catalyst. Embodiment 2 is the catalyst of embodiment 1, wherein the active catalyst has a formula of $Mo_xV_yNb_zPd_nO_m$, where x is in a range of 1 to 5, y is in a range of greater than 0 to 0.5, z is in a range of 0.01 to 0.5, n is in a range of greater than 0 to 0.2 and m is a number determined by the valence requirements of the other elements in the composition. Embodiment 3 is the catalyst of either embodiment 1 or 2, wherein the molybdenum metal-containing compound is ammonium heptamolybdate, sodium molybdate, ammonium orthomolybdate, ammonium paramolybdate, or an acetate, oxalate, mandelate, or glycolate salt, or a combination thereof. Embodiment 4 is the catalyst of any of embodiments 1 to 3, wherein the vanadium metal-containing compound is ammonium metavanadate, sodium metavanadate, sodium decavanadate, or sodium orthovanadate, or an acetate, oxalate, or tartrate salt, or a combination thereof. Embodiment 5 is the catalyst of any of embodiments 1 to 4, wherein the niobium metal containing compound is lithium niobate, potassium niobate, strontium barium niobate, niobium oxalate, niobium oxide, niobium hydrate oxide, or a combination thereof. Embodiment 6 is the catalyst of any of embodiments 1 to 5, wherein the palladium containing compound includes a palladium salt, a palladium complex, palladium on a support, or a combination thereof. Embodiment 7 is the catalyst of any of embodiments 1 to 6, wherein 10 to 500 ppm of palladium is distributed on a surface of the active catalyst. Embodiment 8 is the catalyst of any of embodiments 1 to 7, wherein the agitating is performed at a temperature in a range of 70 to 100° C. Embodiment 9 is the catalyst of any of embodiments 1 to 8, wherein the active catalyst is not supported on a support material. Embodiment 10 is the catalyst of any of embodiments 1 to 9, wherein the drying is performed at a drying temperature of 80 to 300° C. Embodiment 11 is the catalyst of any of embodiments 1 to 8, wherein the calcining is performed by heating to a temperature from 250 to 400° C. Embodiment 12 is the catalyst of embodiment 9, wherein the calcining has a calcination duration of from one to sixteen hours.

Embodiment 13 is a method for oxidizing a $C_2$ hydrocarbon. The method includes reacting the $C_2$ hydrocarbon with an oxidant in the presence of the active catalyst of any of embodiments 1 to 12 to produce an oxidized hydrocarbon. Embodiment 14 is the method of embodiment 13, wherein the $C_2$ hydrocarbon contains ethane and the oxidized hydrocarbon contains acetic acid. Embodiment 15 is the method of either of embodiments 13 or 14, wherein the reacting is performed at a reaction temperature of 200 to 320° C. Embodiment 16 is the method of any of embodiments 13 to 15, wherein the reacting is performed at a reaction pressure of 10 to 35 bar. Embodiment 17 is the method of any of embodiments 13 to 16, wherein the catalyst is disposed in a fixed bed reactor and/or a fluidized bed reactor. Embodiment 18 is the method of any of embodiments 13 to 17, wherein the reacting is performed at a Weight Hourly Space Velocity of 1,000 to 10,000 $hr^{-1}$. Embodiment 19 is the method of any of embodiments 13 to 18, wherein the $C_2$ hydrocarbon in the reacting step has a delta ethane ranging from 0.1 to 10 mol. %.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A catalyst produced by a process, the process comprising:
   (a) combining each of a molybdenum, vanadium, and niobium metal or metal-containing compound in water to form a slurry;
   (b) agitating the slurry for a period of time of at least 15 minutes;
   (c) after at least 15 minutes of agitating the slurry comprising molybdenum, vanadium, and niobium, adding palladium or a palladium-containing compound to the slurry; and
   (d) collecting, drying, and calcining the slurry to obtain an active catalyst.

2. The catalyst of claim 1, wherein the active catalyst has a formula of $Mo_xV_yNb_zPd_nO_m$, where x is in a range of 1 to 5, y is in a range of greater than 0 to 0.5, z is in a range of 0.01 to 0.5, n is in a range of greater than 0 to 0.2 and m is a number determined by the valence requirements of the other elements in the composition.

3. The catalyst of claim 1, wherein the molybdenum metal-containing compound is ammonium heptamolybdate, sodium molybdate, ammonium orthomolybdate, ammonium paramolybdate, or an acetate, oxalate, mandelate, or glycolate salt, or a combination thereof.

4. The catalyst of claim 1, wherein the vanadium metal-containing compound is ammonium metavanadate, sodium metavanadate, sodium decavanadate, or sodium orthovanadate, or an acetate, oxalate, or tartrate salt, or a combination thereof.

5. The catalyst of claim 1, wherein the niobium metal containing compound is lithium niobate, potassium niobate, strontium barium niobate, niobium oxalate, niobium oxide, niobium hydrate oxide, or a combination thereof.

6. The catalyst of claim 1, wherein the palladium containing compound includes a palladium salt, a palladium complex, palladium on a support, or a combination thereof.

7. The catalyst of claim 1, wherein 10 to 500 ppm of palladium is distributed on a surface of the active catalyst.

8. The catalyst of claim 1, wherein the agitating is performed at a temperature in a range of 70 to 100° C.

9. The catalyst of claim 1, wherein the active catalyst is not supported on a support material.

10. The catalyst of claim 1, wherein the drying is performed at a drying temperature of 80 to 300° C.

11. The catalyst of claim 1, wherein the calcining is performed by heating to a temperature from 250 to 400° C.

12. The catalyst of claim 9, wherein the calcining has a calcination duration of from one to sixteen hours.

13. A method for oxidizing a $C_2$ hydrocarbon, the method comprising: reacting the $C_2$ hydrocarbon with an oxidant in the presence of the active catalyst of claim 1 to produce an oxidized hydrocarbon.

14. The method of claim 13, wherein the $C_2$ hydrocarbon comprises ethane and the oxidized hydrocarbon comprises acetic acid.

15. The method of claim 13, wherein the reacting is performed at a reaction temperature of 200 to 320° C.

16. The method of claim 13, wherein the reacting is performed at a reaction pressure of 10 to 35 bar.

17. The method of claim 13, wherein the catalyst is disposed in a fixed bed reactor and/or a fluidized bed reactor.

18. The method of claim 13, wherein the reacting is performed at a Weight Hourly Space Velocity of 1,000 to 10,000 $hr^{-1}$.

19. The method of claim 13, wherein the $C_2$ hydrocarbon in the reacting step has a delta ethane ranging from 0.1 to 10 mol. %.

20. The method of claim 14, wherein the $C_2$ hydrocarbon in the reacting step has a delta ethane ranging from 0.1 to 10 mol. %.

* * * * *